(12) United States Patent
Stahmann et al.

(10) Patent No.: US 7,186,220 B2
(45) Date of Patent: Mar. 6, 2007

(54) IMPLANTABLE DEVICES AND METHODS USING FREQUENCY-DOMAIN ANALYSIS OF THORACIC SIGNAL

(75) Inventors: Jeffrey E. Stahmann, Ramsey, MN (US); Jesse W. Hartley, Lino Lakes, MN (US); Quan Ni, White Bear Lake, MN (US); John Hatlestad, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 505 days.

(21) Appl. No.: 10/612,387

(22) Filed: Jul. 2, 2003

(65) Prior Publication Data

US 2005/0004609 A1 Jan. 6, 2005

(51) Int. Cl.
*A61B 5/08* (2006.01)
(52) U.S. Cl. ............ 600/529; 600/484; 600/547
(58) Field of Classification Search ......... 607/4–6, 607/9, 17–20, 32, 59, 60, 62; 600/519, 526, 600/527, 547, 484, 529
See application file for complete search history.

(56) References Cited

U.S. PATENT DOCUMENTS

| | | | |
|---|---|---|---|
| 4,510,944 A | 4/1985 | Porges | |
| 4,519,395 A | 5/1985 | Hrushesky | |
| 4,858,611 A | 8/1989 | Elliott | |
| 5,003,976 A | 4/1991 | Alt | 128/419 PG |
| 5,074,303 A | 12/1991 | Hauck | 128/419 |
| 5,284,136 A | 2/1994 | Hauck et al. | 607/24 |
| 5,876,353 A | 3/1999 | Riff | 600/547 |
| 5,957,861 A | 9/1999 | Combs et al. | 600/547 |
| 5,974,340 A | 10/1999 | Kadhiresan | 607/18 |
| 6,076,015 A | 6/2000 | Hartley et al. | 607/20 |
| 6,193,668 B1 | 2/2001 | Chassaing et al. | 600/481 |
| 6,223,064 B1 | 4/2001 | Lynn et al. | 600/324 |
| 6,275,727 B1 | 8/2001 | Hopper et al. | |
| 6,411,840 B1 | 6/2002 | Bardy | |
| 6,418,342 B1 * | 7/2002 | Owen et al. | 607/5 |
| 6,459,929 B1 | 10/2002 | Hopper et al. | |

(Continued)

FOREIGN PATENT DOCUMENTS

EP 0555988 8/1993

(Continued)

OTHER PUBLICATIONS

"BioZ(r) ICG Module", http://web.archive.org/web/20010701105207/http://www.cardiodynamics.com/cdprod50.html (archived Jul. 1, 2001), 1 page.

(Continued)

*Primary Examiner*—Robert Pezzuto
*Assistant Examiner*—Yun Haeng Lee
(74) *Attorney, Agent, or Firm*—Schwegman, Lundberg, Woessner, & Kluth, P.A.

(57) ABSTRACT

This document describes, among other things, systems, devices, and methods that use frequency domain analysis of a thoracic signal. One example uses frequency domain analysis for discriminating between different pulmonary physiological states. Examples of breathing states include normal breathing, periodic breathing, Cheyne-Stokes breathing, obstructed respiration, restrictive respiration, and pulmonary edema. The frequency domain analysis may also be used for performing heart rate variability (HRV) diagnostics. In one example, a frequency domain adaptive filter implements a variable cutoff frequency for separating heart contraction spectral content and other spectral content from lower frequency respiration spectral content and other lower frequency spectral content.

56 Claims, 10 Drawing Sheets

U.S. PATENT DOCUMENTS

| | | | |
|---|---|---|---|
| 6,478,746 B2 | 11/2002 | Chassaing et al. | 600/504 |
| 6,520,924 B2 | 2/2003 | Lee | 600/586 |
| 6,561,986 B2 | 5/2003 | Baura et al. | 600/526 |
| 6,575,916 B2 | 6/2003 | Halleck et al. | 600/528 |
| 6,589,188 B1* | 7/2003 | Street et al. | 600/538 |
| 2003/0028221 A1* | 2/2003 | Zhu et al. | 607/9 |
| 2003/0216664 A1* | 11/2003 | Suarez | 600/547 |
| 2005/0065448 A1 | 3/2005 | Stahmann et al. | |
| 2006/0020295 A1 | 1/2006 | Brockway | |

FOREIGN PATENT DOCUMENTS

| | | |
|---|---|---|
| WO | WO-2004012815 A1 | 2/2004 |

OTHER PUBLICATIONS

"BioZ.com(tm) Noninvasive Hemodynamic Monitor", http://web/archive.org/web/20000617081457/http://www.cardiodynamics.com/cdprod10.html (archived Jun. 17, 2000), 2 pages.

"CardioDynamics BioZtect ICG Sensor & Cable System", http://web.archive.org/web/20010701105810/http://www.cardiodynamics.com/cdprod60.html, (archived Jul. 1, 2001), 2 pages.

"CardioDynamics Company Overview", http://web.archive.org/web/20001121133300/http://www.cardiodynamics.com/cdcomp10.html, (archived Nov. 21, 2000), 2 pages.

"Overview of Impedance Cardiography (ICG)", http:/web.archive.org/web/20021003000713/http://www.impedancecariography.com/icgover10.html, (archived Oct. 3, 2002), 5 Pages.

Brockway, M., et al., "Method and Apparatus for Monitoring Heart Failure Patients With Cardiopulmonary Comorbidities", *Application Ser. No. 10/897,856, Filed Jul. 23, 2004*, 54 pages.

Ponikowski, P., et al., "Oscillatory Implications and Role Augmented Peripheral Chemosensitivity", *Circulation*, 100, (1999),2418-2424.

\* cited by examiner

IMPLANTABLE DEVICES AND METHODS USING FREQUENCY-DOMAIN ANALYSIS OF THORACIC SIGNAL

TECHNICAL FIELD

This document relates generally to medical systems, devices, and methods, and particularly, but not by way of limitation, to implantable devices and methods using frequency-domain analysis of a thoracic signal.

BACKGROUND

Implantable cardiac rhythm management devices typically monitor and process heart signals to provide the heart with needed therapy. One example of such therapy includes delivering a pacing pulse that triggers a resulting heart contraction. Another example includes delivering a defibrillation shock that interrupts an abnormal heart rhythm. Some cardiac rhythm management devices also monitor the patient's breathing (also referred to as the patient's respiration). Such devices typically use breathing to control the delivery of pacing pulses to increase the patient's heart rate when the patient breathes more rapidly, and to slow the patient's heart rate when the patient breathes more slowly.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

FIGS. 3A, 3B, and 3C jointly provide a generalized conceptual illustration of normal breathing.

DETAILED DESCRIPTION

In the following detailed description, reference is made to the accompanying drawings, which form a part hereof, and in which is shown by way of illustration specific embodiments in which the invention may be practiced. These embodiments, which are also referred as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management devices such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

The present inventors have recognized that certain sicknesses also affect pulmonary function or both pulmonary and cardiac function, and that there exists an unmet need for providing improved systems, devices, and methods for using information obtained from the patient's pulmonary function or both pulmonary and cardiac function to provide better diagnosis and/or treatment of certain patients and/or for determining therapy efficacy.

Figure 1:
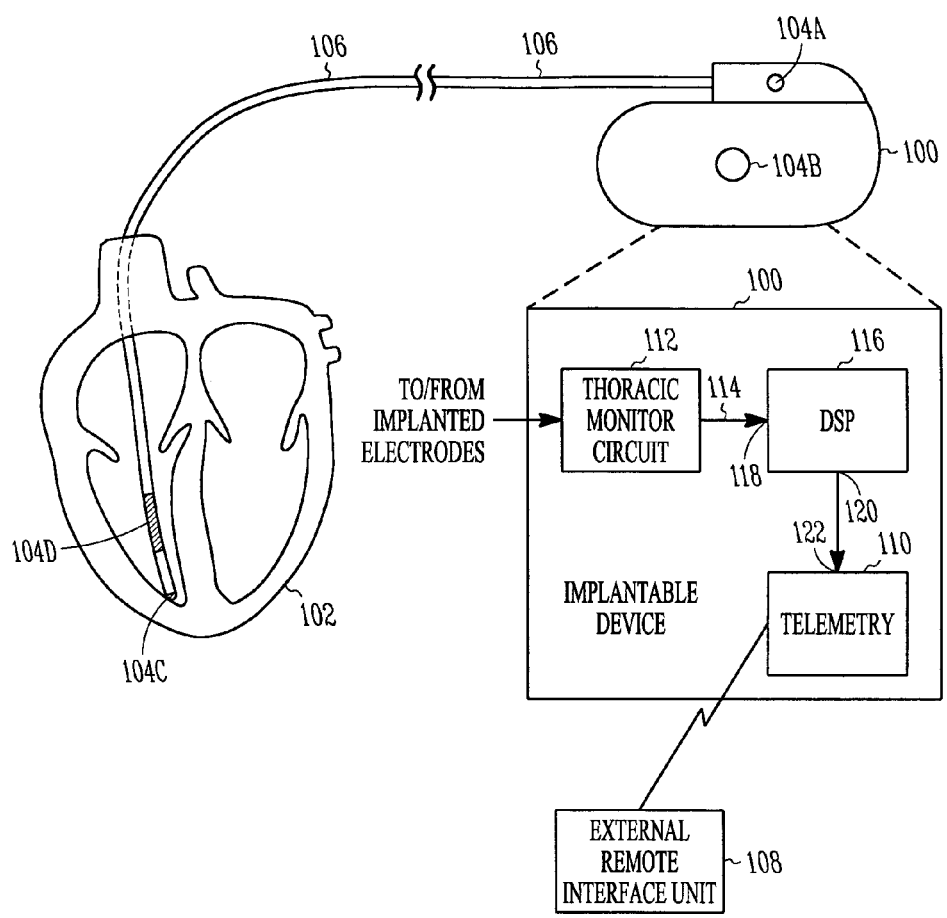
FIG. 1 is a schematic diagram illustrating generally one example of portions of an implantable unit, such as implantable cardiac rhythm management device.

FIG. 1 is a schematic diagram illustrating generally, by way of example, but not by way of limitation, portions of an implantable unit, such as implantable cardiac rhythm management device 100. The example of FIG. 1 also illustrates portions of one environment in which the device 100 is capable of being used. In the example illustrated in FIG. 1, the implantable unit 100 is operatively coupled to the subject's heart 102 and to a portion of the subject's thorax using implantable electrodes 104. The electrodes 104 are located with the device 100 and/or are located in association with the heart, such as by being disposed on the distal end of an intravascular leadwire 106 that is coupled to the device 100. The example of FIG. 1 also illustrates an external remote interface unit 108. In this example, the remote interface unit 108 is located external to the subject. The remote interface unit 108 is wirelessly or otherwise communicatively coupled to a telemetry circuit 110 included in the implantable device 100.

In the example of FIG. 1, the device 100 includes a thoracic monitor circuit 112. As discussed below, one example of the thoracic monitor circuit 112 includes an impedance detector circuit. Another example of the thoracic monitor circuit 112 includes an acceleration detector circuit. In the example in which the thoracic monitor circuit 112 includes an impedance detector circuit, the impedance detector circuit is configured to use the implanted electrodes 104 to detect a transthoracic impedance associated with a portion of the subject's thorax. One suitable electrode configuration for detecting transthoracic impedance is described in commonly-assigned Hartley et al. U.S. Pat. No. 6,076,015 entitled RATE ADAPTIVE CARDIAC RHYTHM MANAGEMENT DEVICE USING TRANSTHORACIC IMPEDANCE, which is incorporated herein by reference in its entirety, including its description of an electrode configuration and circuitry to detect transthoracic impedance. Another suitable electrode configuration for detecting transthoracic impedance is described in commonly-assigned Hauck et al. U.S. Pat. No. 5,284,136 entitled DUAL INDIFFERENT ELECTRODE PACEMAKER, which is incorporated herein by reference in its entirety, including its description of an electrode configuration and circuitry to detect transthoracic impedance. The electrode configuration need not use a header electrode 104A. In different examples, the electrode configuration includes two electrodes 104, three electrodes 104, and four electrodes 104.

The thoracic monitor circuit 112 includes an output 114 to provide a thoracic signal. The thoracic signal provided at the output 114 includes information about the subject's thoracic impedance and/or acceleration. Such thoracic information provides information about the subject. For example, one component of such thoracic information provides information about the subject's heart contractions, including information about the rate at which such atrial and/or ventricular heart contractions occur. Another component of such thoracic information provides information about the subject's breathing or respiration.

In the example of FIG. 1, the device 100 also includes a digital signal processor (DSP) circuit 116. The DSP circuit 116 includes an input 118 that is coupled to the output 114 of the thoracic monitor circuit 112 to receive a digitized thoracic signal provided by the thoracic monitor circuit 112. As discussed below, the DSP circuit 116 performs frequency domain signal processing on the thoracic signal. One example of such frequency domain signal processing includes separating cardiac contraction information from lower frequency components of the thoracic signal. Another example of such frequency domain signal processing includes extracting respiration information from the thoracic signal. In a further example, the DSP circuit 116 uses spectral analysis to classify the subject's pulmonary physiological state. The DSP circuit 116 includes an output 120 that provides information about the subject, for example, information about the pulmonary physiological classification. In a further example, the telemetry circuit 110 includes an input 122 that is coupled to the output 120 of the DSP circuit 116 to receive an indication of the pulmonary physiological classification or the like. In this example, the telemetry circuit 110 is capable of communicating at least one indication of the pulmonary physiological classification to the external remote interface unit 108, for external storage and/or display, either of a single such indication instance or of a trend of such indication instances.

Figure 2:
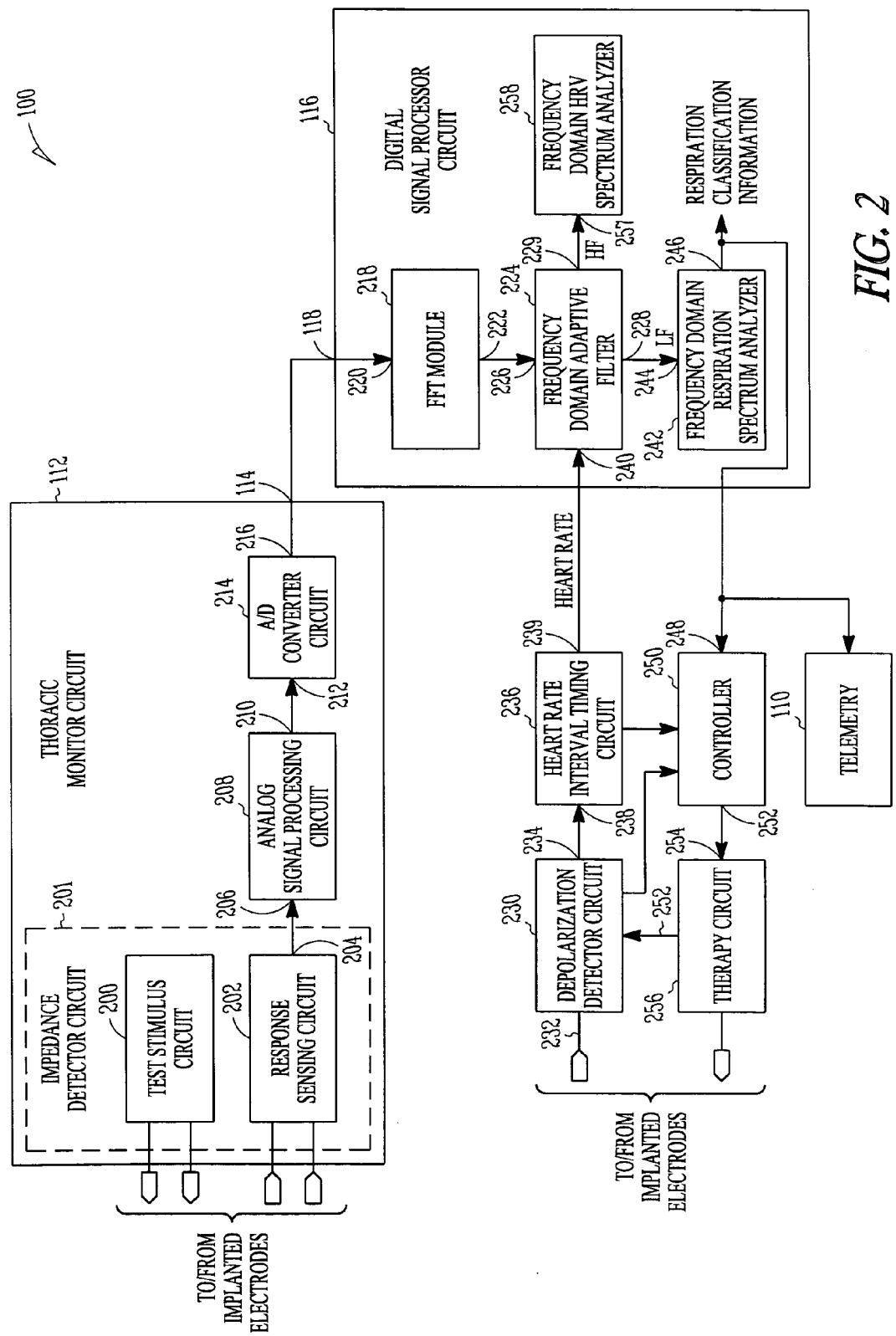
FIG. 2 is a schematic diagram illustrating generally further details of portions of one example of the implantable device.

FIG. 2 is a schematic diagram illustrating generally, by way of example, but not by way of limitation, further details of portions of one example of the implantable device 100. In the example of FIG. 2, the thoracic monitor circuit 112 includes an impedance detecting circuit 201, comprising a test stimulus circuit 200 to provide an excitation or stimulus to a portion of the subject's thorax for detecting transthoracic impedance. The impedance detecting circuit 201 also includes a response sensing circuit 202 to sense a responsive indication correlative to transthoracic impedance. In one example, the test stimulus circuit 200 includes a test current carrier signal generator, and the response sensing circuit 202 includes a voltage preamplifier circuit, such as described in detail in Hartley et al. U.S. Pat. No. 6,076,015, which is incorporated by reference herein in its entirety, including its description of an exciter circuit and a preamplifier circuit.

In the example illustrated in FIG. 2, at least one output 204 of the response sensing circuit 202 is coupled to at least one input 206 of an analog signal processing circuit 208. In one example, the analog signal processing circuit 208 includes, among other things, a demodulator circuit and a bandpass filter circuit, such as described in detail in Hartley et al. U.S. Pat. No. 6,076,015, which is incorporated by reference herein in its entirety, including its description of demodulator and bandpass filter circuits. In the example of FIG. 2, an output 210 of the analog signal processing circuit 208 is coupled to an input 212 of an analog-to-digital (A/D) converter circuit 214, such as the 8-bit A/D converter described in Hartley et al. U.S. Pat. No. 6,076,015, which is incorporated by reference herein in its entirety, including its description of an A/D converter circuit. At least one output 216 of the A/D converter circuit 214 is coupled to the output 114 of the thoracic monitor circuit 112 to provide a digitized thoracic signal coupled by a bus connection or otherwise to the input 118 of the DSP circuit 116.

In the example of FIG. 2, the DSP circuit 116 includes a time-domain-to-frequency-domain conversion circuit, such as fast Fourier transform (FFT) module 218. The FFT module 218 may be implemented either as a dedicated hardware circuit or as a sequence of instructions executed on a microprocessor circuit or the like. The FFT module 218 includes an input 220 that is coupled to the input 118 of the DSP circuit 116 to receive the digitized time-domain thoracic signal provided by the thoracic monitor circuit 112. In this example, the FFT module 218 converts the digitized time-domain thoracic signal received from the thoracic monitor circuit 112 into a digitized frequency-domain thoracic signal provided at an output 222 of the FFT module 218.

In the example of FIG. 2, the DSP circuit 116 includes a frequency-domain filter 224. The filter 224 may be implemented either as a dedicated hardware circuit or as a sequence of instructions executed on a microprocessor circuit or the like. An input 226 of the frequency-domain filter 224 is coupled to the output 222 of the FFT module 218 to receive the frequency-domain thoracic signal. In one example, the frequency-domain filter 224 extracts a frequency-domain respiration signal from the frequency-domain thoracic signal (which may also include confounding signal content, such as a higher frequency heart contraction component, and such as a lower frequency component due to fluid shifts toward or away from the thorax). The filter 224 provides the resulting frequency-domain respiration signal at an output 228.

In the example of FIG. 2, the frequency domain filter 224 is implemented as an adaptive frequency-domain filter 224 in which a filter cutoff frequency varies according to a detected heart rate. In this example, the device 100 includes at least one sense amplifier or other such depolarization detector circuit 230. The depolarization detector circuit 230 includes inputs 232 that are coupled to the implanted electrodes to detect heart depolarizations indicative of heart contractions. The depolarization detector circuit 230 includes one or more outputs 234 providing interrupts triggered by such detected heart depolarizations. A heart rate interval timer circuit 236 includes one or more corresponding inputs 238 coupled to the respective outputs 234 of the depolarization detector circuit 230 to receive the interrupts. The heart rate interval timer circuit 236 computes the time interval between interrupts indicating heart depolarizations. An output 239 of the heart rate interval timer circuit 236 provides information correlative to the heart rate frequency between successive heart contractions to an input 240 of the frequency-domain adaptive filter 224. In response to such heart rate information, the frequency-domain adaptive filter 224 adjusts a cutoff frequency in the frequency domain. In one example, this heart-rate dependent variable cutoff frequency is used for separating, in the frequency domain, heart contraction information from respiration information, such as to obtain a frequency-domain signal correlative to the subject's heart contractions and respiration, respectively. In this example, heart contraction information is provided at output 229 of the filter 224. Respiration information is provided at the output 228 of the filter 224.

In the example of FIG. 2, the DSP circuit 116 includes a frequency-domain spectrum analyzer 242. The spectrum analyzer 242 may be implemented either as a dedicated hardware circuit or as a sequence of instructions executed on a microprocessor circuit or the like. The spectrum analyzer 242 includes an input 244 that is coupled to receive the frequency domain respiration signal from the output 228 of the filter 224. In one example, the spectrum analyzer 242 classifies the subject's respiration using frequency domain spectrum analysis of the frequency domain respiration signal. An output 246 of the spectrum analyzer 242 provides a resulting digitally encoded pulmonary physiological state classification signal (e.g., normal breathing, periodic breathing, Cheyne-Stokes breathing, obstructed respiration, restrictive respiration, pulmonary fluid accumulation, etc.) In one example, this pulmonary physiological classification is communicated to the telemetry circuit 110, for further communication from the subject to the external remote interface unit, such as for assisting a caregiver in diagnosing at least one aspect of the subject's health status. In another example, the pulmonary physiological classification is communicated to an input 248 of a controller 250. The controller 250 includes one or more outputs 252 that are coupled to corresponding inputs 254 of a therapy circuit 256, such as for controlling its delivery of pacing, defibrillation, resynchronization or other cardiac rhythm management therapy provided to the subject using implanted electrodes. In one example, the controller 250 adjusts the cardiac rhythm management therapy using, among other things, the pulmonary physiological classification information.

In one further variation of the above system 100, the DSP circuit 116 also includes a frequency domain heart rate variability (HRV) spectrum analyzer circuit 258 for processing heart contraction information received at an input 257 from the output 229 of the frequency domain adaptive filter 224. This embodiment is discussed further below.

Figure 3A:
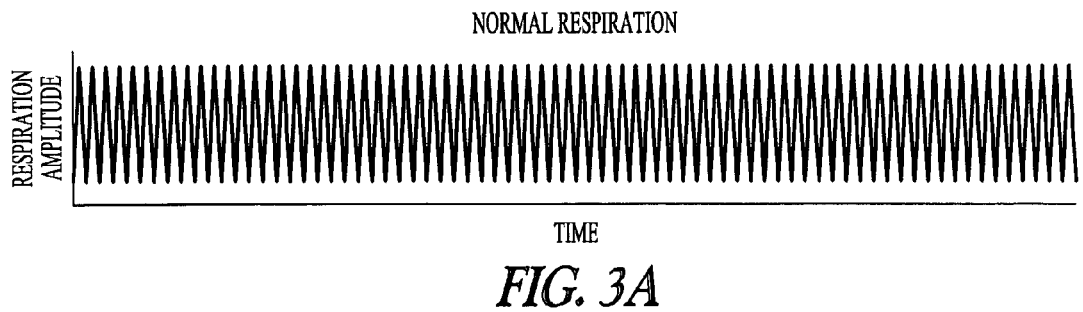
Figure 3B:
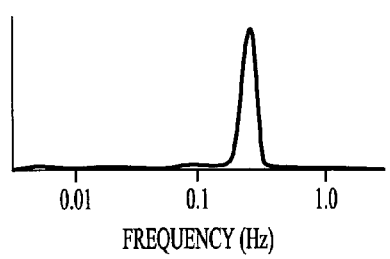

FIGS. 3A, 3B, and 3C jointly provide a generalized conceptual illustration of normal breathing. FIG. 3A illustrates a conceptual example of a time domain normal respiration signal, illustrating respiration amplitude vs. time. FIGS. 3B and 3C provide corresponding spectral illustrations (amplitude vs. frequency) of this normal respiration signal after being converted into the frequency domain. In this example, normal respiration is characterized by a respiration rate of between about 5 breaths per minute and about 20 breaths per minute, when the subject is at rest. However, when the subject is exercising, the respiration rate will typically be between about 15 breaths per minute and about 60 breaths per minute. FIG. 3B illustrates an idealized frequency spectrum, for the resting subject, having the energy concentrated at about 0.17 Hz (i.e., about 10 breaths per minute), and assumes pure sinusoidal respiration at a fixed rate. FIG. 3C illustrates the frequency spectrum of a more likely encountered respiration signal that is not a pure sinusoid and includes some variation in the respiratory rate.

Figure 4A:
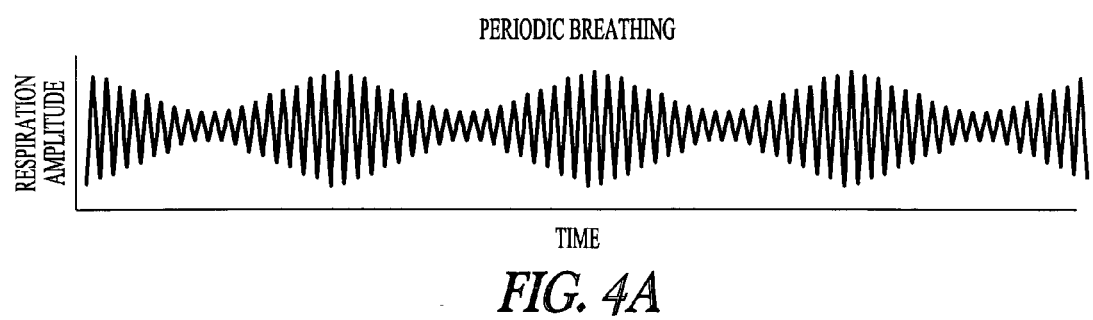
FIGS. 4A, 4B, and 4C jointly provide a generalized conceptual illustration of periodic breathing.
Figure 4B:
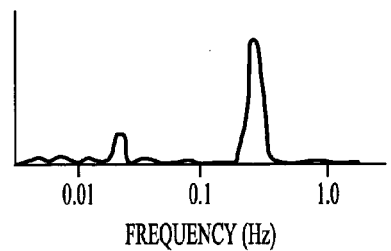
Figure 4C:
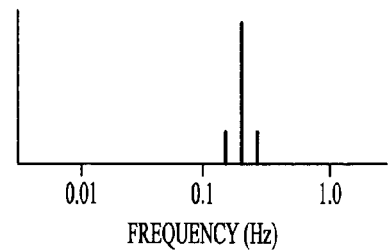

FIGS. 4A, 4B, and 4C jointly provide a generalized conceptual illustration of periodic breathing. FIG. 4A illustrates a conceptual example of a time-domain periodic respiration signal, illustrating respiration amplitude vs. time. FIGS. 4B and 4C provide corresponding spectral illustrations (amplitude vs. frequency) of this periodic respiration signal after being converted into the frequency domain. In this example, periodic respiration is characterized by a modulation in breathing amplitude. The modulation typically exhibits a period between about 0.5 minutes and about 2 minutes. FIG. 4B illustrates the idealized resulting frequency spectrum, for the resting subject, having most energy concentrated at about 0.17 Hz (i.e., about 10 breaths per minute), but also having considerable energy concentrated at about 0.167 Hz−0.017 Hz=0.150 Hz and at about 0.167 Hz+0.017 Hz=0.184 Hz (i.e., at the breathing frequency of about 1 cycle per minute, corresponding to the modulation frequency).

Figure 5A:
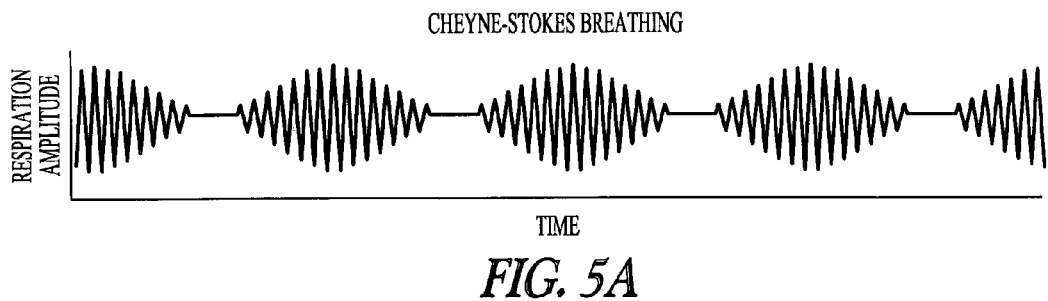
FIGS. 5A, 5B, and 5C jointly provide a generalized conceptual illustration of Cheyne-Stokes breathing.
Figure 5B:
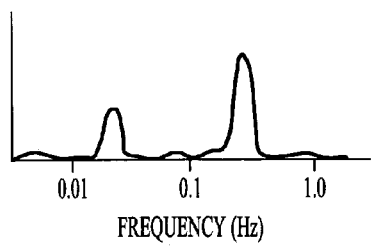
Figure 5C:
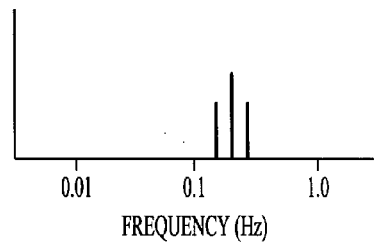

FIGS. 5A, 5B, and 5C jointly provide a generalized conceptual illustration of Cheyne-Stokes breathing. FIG. 5A illustrates a conceptual example of a time-domain Cheyne-Stokes respiration signal, illustrating respiration amplitude vs. time. FIGS. 5B and 5C also illustrate a corresponding spectral illustration (amplitude vs. frequency) of this Cheyne-Stokes respiration signal after being converted into the frequency domain. In this example, Cheyne-Stokes respiration is characterized by a modulation in breathing amplitude, similar to that illustrated in FIG. 4 for periodic breathing. The modulation typically exhibits a period of between about 0.5 minutes and about 2 minutes. However, unlike periodic breathing, the modulation that occurs in Cheyne-Stokes breathing results in the respiration amplitude going to zero during the "valleys" of the modulated respiration signal, as illustrated in FIG. 5A. FIGS. 5B and 5C illustrate the resulting frequency spectrum for the resting subject. Like the case of periodic breathing, most of the spectral energy illustrated in Cheyne-Stokes breathing of FIGS. 5A and 5B is concentrated at about 0.17 Hz (i.e., about 10 breaths per minute). Moreover, the Cheyne-Stokes breathing of FIGS. 5B and 5C includes even less energy concentrated at 0.167 Hz than for the case of periodic breathing.

The idealized spectrums shown in FIG. 4B and FIG. 5B represent a respiration signal that is purely sinusoidal and at a constant rate. FIG. 4B and FIG. 5B also represent a modulation signal (i.e., the periodic breathing) that is purely sinusoidal, where the modulation of the respiratory signal by periodic breathing can be represented by a purely multiplicative process. FIG. 4C and FIG. 5C illustrate the frequency spectrum of a more likely encountered periodic respiration and Cheyne-Stokes respiration, respectively. FIG. 4C and FIG. 5C represent modulation signals that are not pure sinusoids and also assumes some variation in respiratory rate. In addition, energy is shown in FIG. 4C and FIG. 5C at the periodic breathing frequency (i.e., about 1 cycle per minute) due to an additive modulation of the respiration signal by the periodic breathing signal. Finally, FIG. 4C and FIG. 5C illustrate a merging of the numerous frequency components around 0.167 Hz due to finite resolution of the spectral analysis apparatus.

Figure 6:
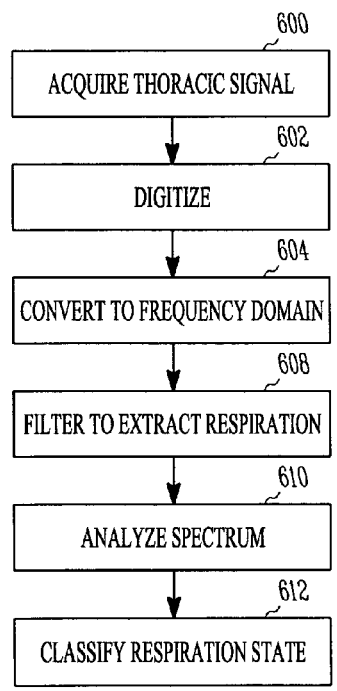
FIG. 6 is a flow chart illustrating generally one technique for using the implantable device for classifying a subject's respiration state.

FIG. 6 is a flow chart illustrating generally, by way of example, but not by way of limitation, one technique for using the device 100 for classifying a subject's respiration state. At 600, a thoracic signal is acquired by the thoracic monitor circuit 112, such as by using the techniques that are described in detail in Hartley et al. U.S. Pat. No. 6,076,015, which is incorporated by reference herein in its entirety, including its description of techniques for acquiring a transthoracic impedance signal. At 602, the thoracic signal is digitized, such as by the A/D converter circuit 214. At 604, the digitized time-domain thoracic signal is converted into a frequency-domain thoracic spectral signal, such as by using the FFT module 218. At 608, a frequency domain filtering is performed to extract the respiration spectral components of the thoracic spectrum. At 610, this resulting respiration spectrum is analyzed in the frequency-domain, such as to obtain information about the subject's respiration state. At 612, the respiration state is classified using information obtained from the frequency-domain analysis of the respiration spectrum.

One consideration in performing the time-domain-to-frequency-domain conversion of 604 is in selecting the appropriate time window of the time domain thoracic signal for converting into a frequency domain thoracic spectral signal (e.g., by performing an FFT) for subsequent analysis of respiration spectral information. In one example, a short term analysis of respiration is desired (e.g., a time window that includes several breaths, and up to about 1 minute, or several minutes). This example permits determining the pulmonary physiological state of the subject. For example, it allows discrimination between normal breathing, periodic breathing, and Cheyne-Stokes breathing, etc. In another example, however, a longer term analysis of respiration is desired. In one such example, the time window may include days or even months. This longer term analysis of respiration may be used to determine the pulmonary physiological state of the subject, such as described above, over the longer term period. Alternatively, such longer term analysis may be used to provide a more generalized indication of the patient's health status. In one such example of a generalized patient health status indicator, a wide respiration spectral dispersion with a predominance of low frequency energy is used as an indicator of a relatively healthy state, while a narrow respiration spectral dispersion with relatively high frequency energy is used as an indicator of a relatively unhealthy state. In another example, substantially continuous high rate breathing, particularly with a low tidal volume (amplitude), will provide a sensitive indication of pulmonary fluid accumulation, also referred to as pulmonary edema.

Figure 7:
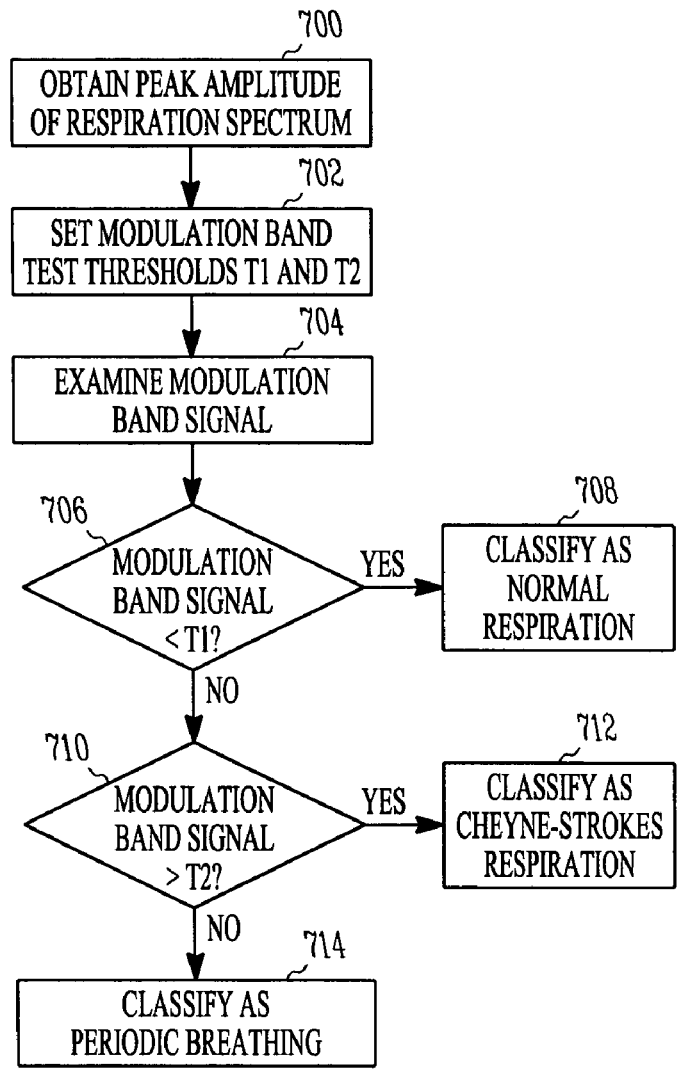
FIG. 7 is a flow chart illustrating generally one technique for analyzing the respiration spectrum.

FIG. 7 is a flow chart illustrating generally, by way of example, but not by way of limitation, one technique for analyzing the respiration spectrum, such as illustrated at 610 of FIG. 6. In FIG. 7, at 700, a peak amplitude of the frequency-domain respiration spectral signal is obtained. In one example, the frequency corresponding to this peak amplitude is also obtained. At 702, modulation band test thresholds T1 and T2 are obtained using the spectrum analyzer 242. In one example, the test thresholds T1 and T2 are spectral amplitudes that are normalized (e.g., a specified percentage) to the previously-obtained peak amplitude of the respiration spectrum. In another example, the test thresholds T1 and T2 are energy thresholds that are normalized (e.g., a specified percentage) to a spectral energy that is obtained by actually or approximately integrating a spectral energy density over a spectral interval [f1, f2] about the frequency ($f_o$) of the peak amplitude.

At 704, the modulation band (e.g., breathing at frequencies having corresponding periods between about 0.5 minutes and about 2 minutes, as discussed above) spectral signal is examined. For the case in which the test thresholds T1 and T2 include spectral amplitudes, then the examination of the modulation band at 704 includes determining a peak amplitude in the modulation band. For the case in which the test thresholds T1 and T2 include energy thresholds, then the examination of the modulation band at 704 includes integrating the spectral energy across the frequencies in the spectral interval [f3, f4] of the modulation band.

At 706, the modulation band signal is compared to the first threshold T1. If the modulation band peak amplitude is less than the amplitude threshold T1 (or, alternatively, the integrated spectral energy in the modulation band is less than the energy threshold T1), then at 708, the respiration state is classified as normal respiration.

Otherwise, at 710, the modulation band signal is compared to the second threshold T2 (which has a greater magnitude than the threshold T1). If the modulation band peak amplitude exceeds the amplitude threshold T2 (or, alternatively, the integrated spectral energy in the modulation band exceeds the energy threshold T2), then, at 712, the respiration state is classified as Cheyne-Stokes respiration. Otherwise, at 714, the respiration state is classified as periodic breathing.

Figure 3B:
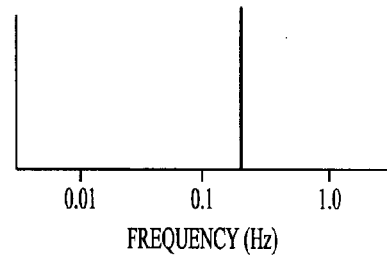
Figure 8:
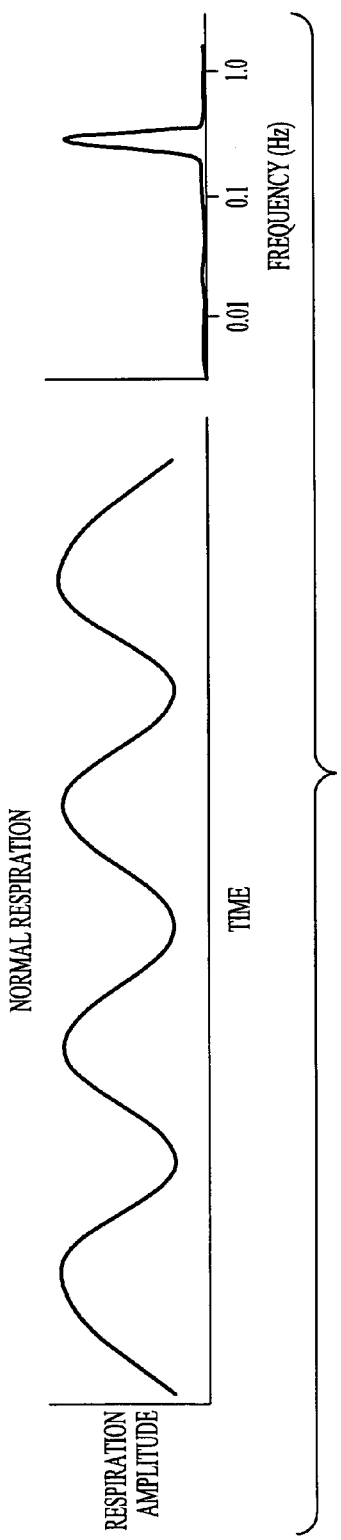
FIG. 8 is another generalized conceptual illustration of normal breathing.
Figure 9:
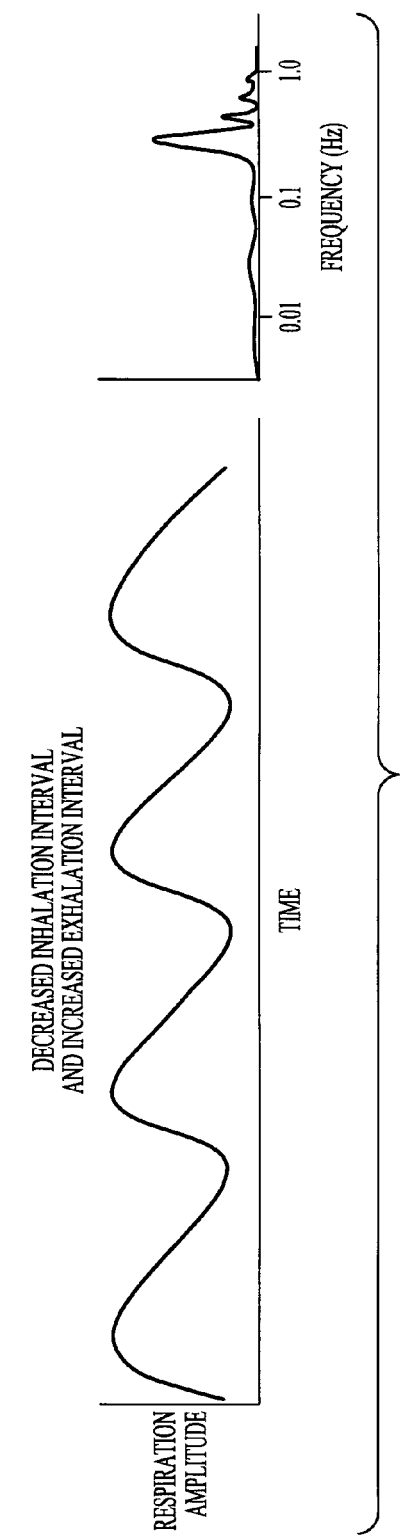
FIG. 9 is a generalized conceptual illustration of an abnormal respiration state, which exhibits shortened inhalation and prolonged exhalation.

FIG. 8 is a generalized conceptual illustration of normal breathing, similar to FIG. 3, but illustrating a higher time-domain resolution. FIG. 9 is a generalized conceptual illustration of another abnormal respiration state (with a time-domain resolution comparable to FIG. 8). The abnormal respiration state of FIG. 9 exhibits decreased inhalation time (a steeper slope on the rising "inhalation" portion of the transthoracic impedance signal), and an increased exhalation time (a more gradual descent on the falling "exhalation" portion of the transthoracic impedance signal). Acutely, this may result from an asthma episode. Chronically, this may result from pulmonary obstructive disease (such as asthma, emphysema, and/or bronchitis). The time-domain abnormal respiration signal illustrated in FIG. 9 results in harmonic content occurring at a higher "harmonic" sideband frequency than the peak amplitude frequency $f_o$ of about 0.17 Hz. By contrast, a restrictive respiration disease (such as pectus excavatum, myasthenia gravis, diffuse idiopathic interstitial fibrosis, and space occupying lesions such as tumors and/or effusions) is characterized by a reduced tidal volume, which results in a reduced spectral amplitude than for normal breathing, and faster breathing, which shifts the spectral content of the respiration signal to a higher frequency than for normal breathing.

Figure 10:
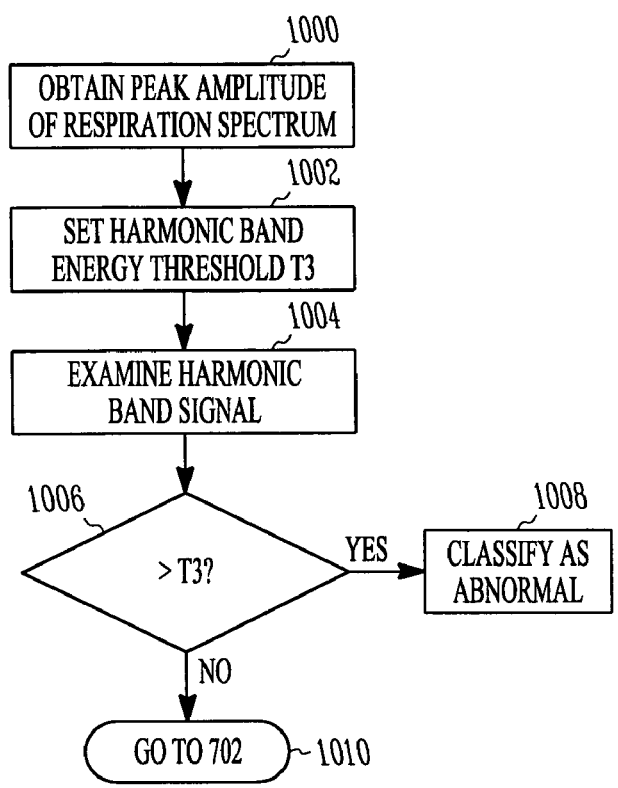
FIG. 10 is a flow chart illustrating generally one technique of performing frequency domain spectral analysis on the respiration spectral signal, such as to distinguish the abnormal respiration state of FIG. 9 from the normal respiration state of FIG. 8.

FIG. 10 is a flow chart illustrating generally, by way of example, but not by way of limitation, one technique of performing frequency domain spectral analysis on the respiration spectral signal, such as to distinguish the abnormal respiration state of FIG. 9 from the normal respiration state of FIG. 8. In the example illustrated in FIG. 10, at 1000, the peak amplitude of the respiration spectral signal is obtained. In one example, the corresponding frequency of such peak amplitude is also obtained. At 1002, a harmonic band energy threshold T3 is obtained using the spectrum analyzer 242. In one example, the test threshold T3 is an energy threshold that is normalized (e.g., a specified percentage) to a spectral energy obtained by actually or approximately integrating a spectral energy density over a spectral interval [f1, f2] about the frequency corresponding to the previously-obtained peak amplitude. At 1004, the harmonic band spectral energy is examined. In one example, the harmonic band spectral energy is obtained by integrating a respiration spectral energy density from a lower frequency limit f5 (e.g., approximately equal to f2) to a higher frequency limit f6 (e.g., that is approximately equal to the variable lowpass cutoff frequency of the frequency-domain adaptive filter 224). At 1006, the harmonic band spectral energy is compared to the energy threshold T3. If the harmonic band spectral energy exceeds T3, then at 1008 the respiration state is classified as being abnormal (e.g., indicative of the shortened inhalation, prolonged exhalation illustrated in FIG. 9). Otherwise, in one example, at 1010, process flow continues at 702 of the flow chart illustrated in FIG. 7, for further classifying the respiration state, as discussed above.

Figure 11:
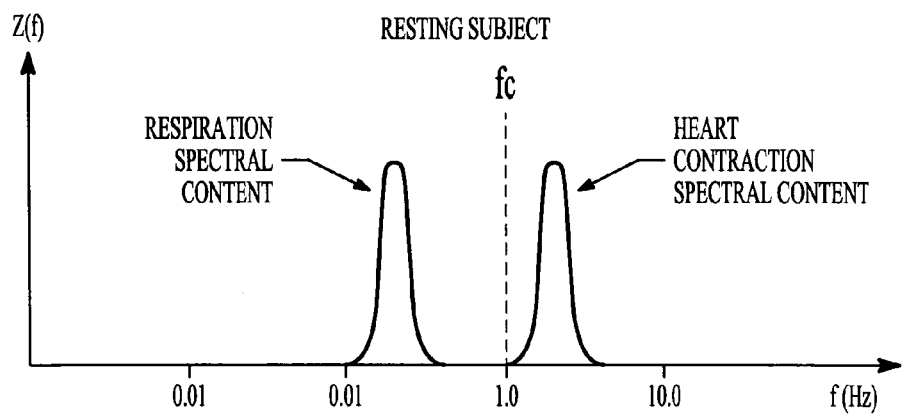
FIG. 11 is a conceptualized graph of a transthoracic impedance spectral signal amplitude vs. frequency for a resting subject.
Figure 12:
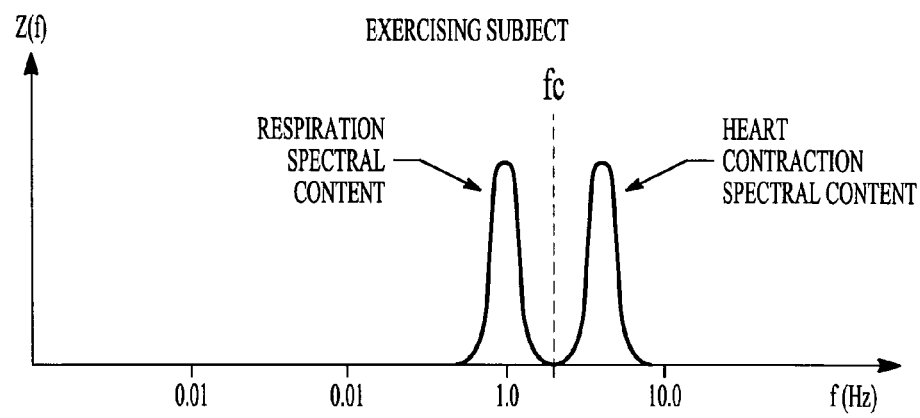
FIG. 12 is a conceptualized graph of a transthoracic impedance spectral signal amplitude vs. frequency for an exercising subject.

FIG. 11 and FIG. 12 are conceptualized graphs of a thoracic spectral signal amplitude vs. frequency for a resting subject and an exercising subject, respectively. As seen by comparing FIG. 11 with FIG. 12, during exercise, the respiration spectral content moves to a higher frequency that is comparable to the frequency of the heart contraction spectral content when the subject is resting. In one example, frequency domain adaptive filter 224 of FIG. 2 includes a variable cutoff frequency $f_c$ that is adjusted as a function of heart rate (HR). The heart rate is obtained from sensed cardiac depolarizations or, for paced depolarizations, from a therapy circuit control signal at 252 that triggers issuance of a contraction-evoking pacing pulse. In one example, the variable cutoff frequency is determined by $f_c$=HR/60−Δ, where Δ is a fixed frequency offset amount and heart rate is expressed in beats per minute. Heart contractions and other spectral content above $f_c$ is, in one example, discarded as noise to the desired respiration spectral content of the thoracic spectral signal.

However, in an alternative example, the heart contraction spectral content is not discarded. Instead, such heart contraction spectral content is provided at the output 229 of the frequency domain adaptive filter to the input 257 of the frequency domain heart rate spectrum analyzer module 258, as illustrated in FIG. 2. The heart rate spectrum analyzer module 258 performs heart rate variability (HRV) diagnostic testing to provide at least one indication of the subject's health status. Examples using spectral analysis of heart beat interval spectral signal information to provide HRV diagnostic information are described in commonly-assigned Spinelli et al. U.S. Pat. No. 5,466,245, Heemels et al. U.S. Pat. No. 5,603,331, Carlson et al. U.S. Pat. No. 6,026,320, and Carlson et al. U.S. Pat. No. 6,301,499, each of which is incorporated herein by reference in its entirety, including their disclosed techniques of using HRV information, such as to provide an indication of a subject's health status.

Figure 13A:
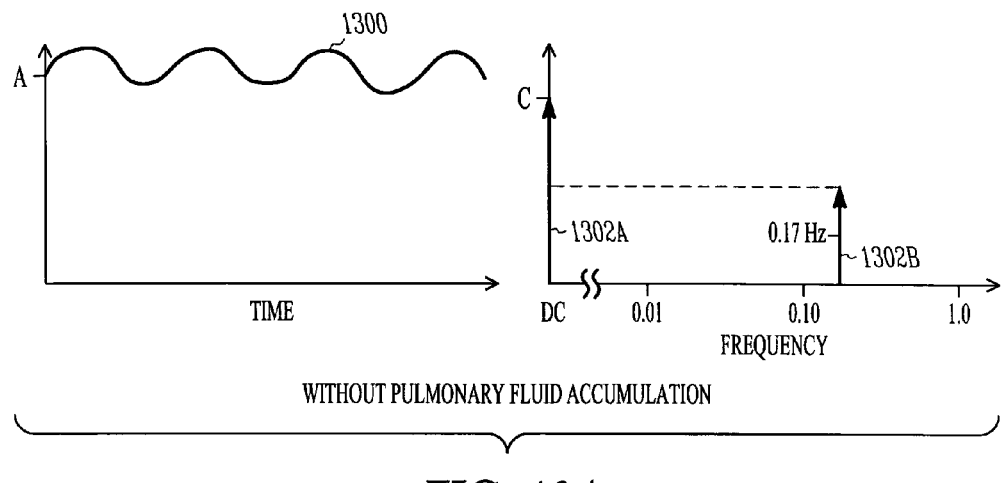
FIG. 13A is a generalized conceptual illustration of a transthoracic impedance signal in the time and frequency domains for a subject without fluid accumulation in or around the lungs.
Figure 13B:
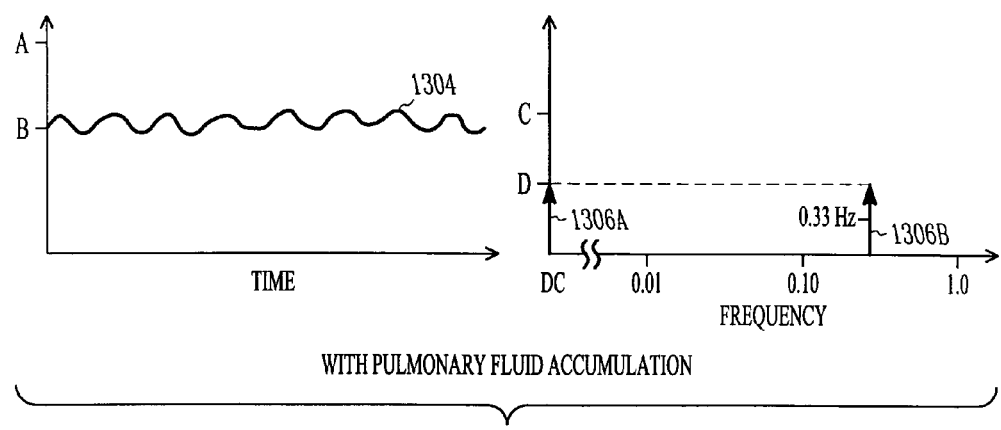
FIG. 13B is a generalized conceptual illustrations of a transthoracic impedance signal in the time and frequency domains for a subject with fluid accumulation in or around the lungs.

FIGS. 13A–13B are a generalized conceptual illustrations of a thoracic impedance signal in the time and frequency domains. FIG. 13A illustrates a time domain thoracic impedance signal 1300 and a frequency domain thoracic impedance signal 1302 in a subject without pulmonary fluid accumulation in (e.g., pulmonary edema) and/or around (e.g., pleural effusion) the lungs. FIG. 13B illustrates a time domain thoracic impedance signal 1304 and a frequency domain thoracic impedance signal 1306 in a subject with pulmonary fluid accumulation in (e.g., pulmonary edema) and/or around (e.g., pleural effusion) the lungs.

As seen in FIGS. 13A–13B, fluid accumulation can have a profound effect on the spectral content of a time-domain thoracic impedance signal. Fluid accumulation will cause a decrease in the substantially DC component 1302A and 1306A (e.g., from C to D, as illustrated in FIG. 13B) of the frequency domain thoracic impedance signal. The fluid accumulation also results in a loss of available lung volume for gas exchange. Therefore, patients with fluid accumulation typically experience rapid, but shallow, breathing. FIGS. 13A–13B illustrates a shift in the higher frequency spectral component 1302B and 1306B from around 0.17 Hz, for the case without fluid accumulation, to around 0.33 Hz, for the case with fluid accumulation. The component 1306B also manifests a lower amplitude, for the case with fluid accumulation, than the component 1302B, for the case without fluid accumulation.

Figure 14:
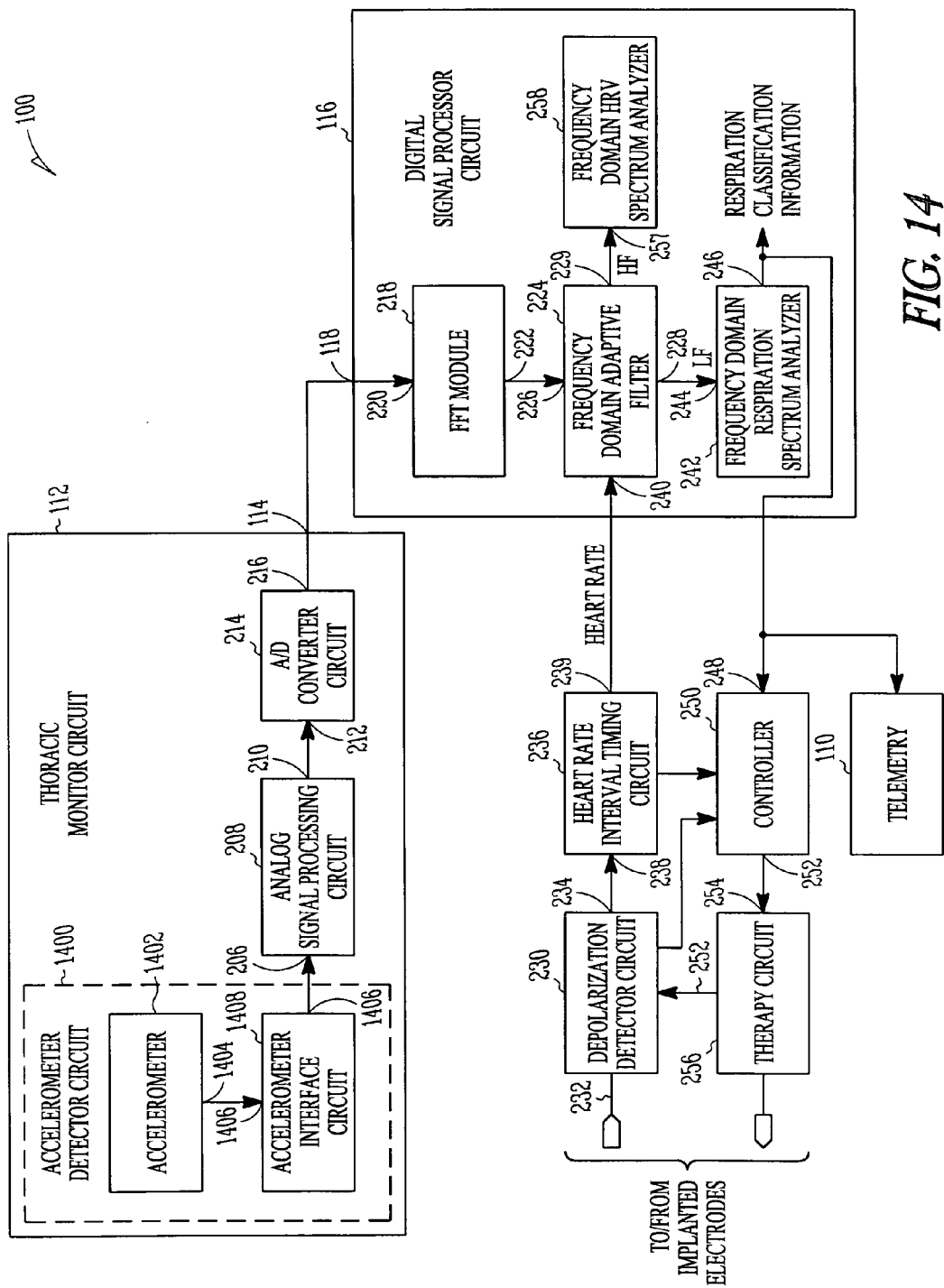
FIG. 14 is a schematic diagram, similar to FIG. 2, but illustrating a thoracic monitor circuit that obtains a thoracic signal from an acceleration detector circuit.

FIG. 14 is a schematic diagram, similar to FIG. 2, but illustrating a thoracic monitor circuit 112 that obtains a thoracic signal from an acceleration detector circuit 1400. The acceleration detector circuit 1400 includes an active or passive accelerometer 1402 or like sensor capable of obtaining respiration and/or heart contraction information from a subject. The accelerometer 1402 includes at least one output 1404 that is coupled to at least one input 1406 of an accelerometer interface circuit 1408. The accelerometer interface circuit 1408 includes at least one output 1410 providing an acceleration-based thoracic signal to the input 206 of the analog signal processing circuit 208. One suitable example of the accelerometer interface circuit 1408, for obtaining an acceleration signal including both respiration and heart contraction information, is described in commonly-assigned Kadhiresan et al. U.S. Pat. No. 5,974,340 entitled APPARATUS AND METHOD FOR MONITORING RESPIRATORY FUNCTION IN HEART FAILURE PATIENTS TO DETERMINE EFFICACY OF THERAPY, which is incorporated herein by reference in its entirety, including its description of interface circuits for use with an accelerometer, such as for obtaining such information.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, the terms "first," "second," "third," etc. are used merely as labels, and are not intended to impose numeric requirements on their objects.

What is claimed is:

1. An apparatus comprising:
an implantable housing, the implantable housing comprising:
a thoracic monitor circuit, including an output to provide time domain thoracic information;
a signal processor circuit, the signal processor circuit comprising:
a time-to-frequency domain converter circuit, including an input coupled to the thoracic monitor circuit output to receive the time domain thoracic information, and including an output providing frequency domain thoracic information; and
a spectrum analyzer circuit, including a input coupled to the time-to-frequency domain converter circuit output to receive the frequency domain thoracic information, and including an output to provide a classification of a pulmonary physiological state using a respiration component of the frequency-domain thoracic information, the classification of the pulmonary physiological state indicative of at least one of pulmonary obstructive disease, a restrictive respiration disease, rapid shallow non-periodic respiration, and respiration having decreased inhalation duration and increased exhalation duration.

2. The apparatus of claim 1, in which the thoracic monitor circuit comprises an impedance detector circuit.

3. The apparatus of claim 2, in which the impedance detector circuit comprises:
a test stimulus circuit, configured to be coupled to a subject using implantable electrodes to deliver a test stimulus to the subject; and
a response sensing circuit, configured to be coupled to the subject using implantable electrodes to receive a signal correlative to transthoracic impedance in the subject in response to the test stimulus delivered to the subject.

4. The apparatus of claim 1, in which the thoracic monitor circuit comprises an acceleration detector circuit.

5. The apparatus of claim 1, in which the thoracic monitor circuit comprises an analog-to-digital (A/D) converter circuit.

6. The apparatus of claim 1, in which the time-to-frequency domain converter circuit comprises a fast-Fourier transform (FET) module.

7. The apparatus of claim 1, further including a telemetry circuit, coupled to the output of the spectrum analyzer to receive the pulmonary physiological state classification for communication from the implantable housing.

8. The apparatus of claim 1, in which the spectrum analyzer is configured to compute a physiological indicator using a heart rate variability (HRV) component of the frequency-domain thoracic information.

9. The apparatus of claim 1, comprising a frequency domain adaptive filter, the frequency domain adaptive filter comprising a first input coupled to the output of the time-to-frequency domain converter circuit, the frequency domain adaptive filter also comprising an output coupled to the input of the spectrum analyzer.

10. The apparatus of claim 9, further comprising:
a depolarization detector circuit; and
a heart rate interval timer circuit, coupled to the depolarization detector circuit, the heart rate interval timer circuit including an output coupled to a second input of the frequency domain adaptive filter.

11. The apparatus of claim 1, in which the signal processor circuit includes a digital signal processor (DSP) circuit.

12. The apparatus of claim 1, comprising:
a controller circuit, the controller circuit comprising an input coupled to the spectrum analyzer output to receive the pulmonary physiological state classification; and
a therapy circuit, coupled to the controller circuit, to deliver therapy to the subject using the pulmonary physiological state classification to control the delivery of therapy.

13. An apparatus comprising:
an implantable housing, the implantable housing comprising:
a thoracic monitor circuit, including an output to provide time domain thoracic information; and
a signal processor circuit, the signal processor circuit comprising:
a time-to-frequency domain converter circuit, including an input coupled to the thoracic monitor circuit output to receive the time domain thoracic information, and including an output providing frequency domain thoracic information; and
a frequency domain adaptive filter, the frequency domain adaptive filter including a first input coupled to the output of the time-to-frequency domain converter circuit, the frequency domain adaptive filter including a second input to receive a time domain heart rate signal, the frequency domain adaptive filter configured to distinguish a respiration component of the frequency domain thoracic information from a heart contraction component of the frequency domain thoracic information to provide a classification of a pulmonary physiological state using a respiration component of the frequency-domain thoracic information, the classification of the pulmonary physiological state indicative of at least one of pulmonary obstructive disease, a restrictive respiration disease, rapid shallow non-periodic respiration, and respiration having decreased inhalation duration and increased exhalation duration.

14. The apparatus of claim 13, in which the thoracic monitor circuit comprises an impedance detector circuit.

15. The apparatus of claim 14, in which the impedance detector circuit comprises:
a test stimulus circuit, configured to be coupled to a subject using implantable electrodes to deliver a test stimulus to the subject; and
a response sensing circuit, configured to be coupled to the subject using implantable electrodes to receive a signal correlative to transthoracic impedance in the subject in response to the test stimulus delivered to the subject.

16. The apparatus of claim 13, in which the thoracic monitor circuit comprises an acceleration detector circuit.

17. The apparatus of claim 13, in which the thoracic monitor circuit comprises an analog-to-digital (A/D) converter circuit.

18. The apparatus of claim 13, in which the time-to-frequency domain converter circuit comprises a fast-Fourier transform (FFT) module.

19. The apparatus of claim 13, in which the signal processor circuit comprises a spectrum analyzer circuit, the spectrum analyzer circuit including a input coupled to the time-to-frequency domain converter circuit output to receive the frequency domain thoracic information, and the spectrum analyzer including an output to provide a classification of a pulmonary physiological state using a respiration component of the frequency-domain thoracic information.

20. The apparatus of claim 19, further comprising:
a controller circuit, the controller circuit including an input coupled to the spectrum analyzer output to receive the pulmonary physiological state classification; and
a therapy circuit, coupled to the controller circuit, to deliver therapy to the subject using the pulmonary physiological state classification.

21. The apparatus of claim 19, further comprising a telemetry circuit, coupled to the output of the spectrum analyzer to receive the pulmonary physiological state classification for communication from the implantable housing.

22. The apparatus of claim 19, in which the spectrum analyzer computes a physiological indicator using a heart rate variability (HRV) component of the frequency-domain thoracic information.

23. The apparatus of claim 13, further comprising:
a depolarization detector circuit; and
a heart rate interval timer circuit, coupled to the depolarization detector circuit, the heart rate interval timer circuit including an output coupled to a second input of the frequency domain adaptive filter.

24. The apparatus of claim 13, in which the signal processor circuit includes a digital signal processor (DSP) circuit.

25. A method comprising:
detecting a time domain thoracic signal using an implanted device;
transforming the time domain thoracic signal into a frequency-domain thoracic signal;
filtering the frequency domain thoracic signal in the frequency domain to obtain frequency domain respiration information; and
classifying a pulmonary physiological state to be indicative of at least one of pulmonary obstructive disease, a restrictive respiration disease, rapid shallow non-periodic respiration, and respiration having decreased inhalation duration and increased exhalation duration.

26. The method of claim 25, in which the detecting the time domain thoracic signal comprises detecting an impedance.

27. The method of claim 25, in which the detecting the time domain thoracic signal comprises detecting an acceleration.

28. The method of claim 25, in which the transforming the time domain thoracic signal comprises using the implanted device.

29. The method of claim 25, in which the filtering comprises using the implanted device.

30. The method of claim 25, in which the classifying a pulmonary physiological state includes using the implanted device.

31. The method of claim 25, in which the transforming the time domain thoracic signal comprises performing a fast Fourier transform (FET).

32. The method of claim 25, in which the classifying the pulmonary physiological state includes classifying the pulmonary physiological state as indicative of normal respiration.

33. The method of claim 25, in which the classifying the pulmonary physiological state includes classifying the pulmonary physiological state as indicative of periodic respiration.

34. The method of claim 25, in which the classifying the pulmonary physiological state includes classifying the pulmonary physiological state as indicative of Cheyne-Stokes respiration.

35. The method of claim 25, in which the classifying the pulmonary physiological state includes classifying the pulmonary physiological state as indicative of obstructed respiration.

36. The method of claim 25, in which the classifying the pulmonary physiological state includes classifying the pulmonary physiological state as indicative of restrictive respiration.

37. The method of claim 25, in which the classifying the pulmonary physiological state includes classifying the pulmonary physiological state as indicative of pulmonary fluid accumulation.

38. The method of claim 25, further comprising communicating information about the pulmonary physiological state from the subject to a remote interface.

39. The method of claim 38, further comprising storing the pulmonary physiological state for a predetermined time in a non-implanted memory.

40. The method of claim 39, further comprising displaying a trend of stored pulmonary physiological states.

41. The method of claim 25, comprising classifying a pulmonary physiological state as rapid shallow non-periodic respiration using the frequency domain respiration information.

42. The method of claim 25, comprising classifying a pulmonary physiological state as respiration having increased inhalation duration and decreased exhalation duration using the frequency domain respiration information.

43. A method comprising:
detecting a time domain thoracic signal using an implanted device;
detecting a heart rate;
transforming the time domain thoracic signal into a frequency domain thoracic signal; and
filtering the frequency domain thoracic signal in the frequency domain using a cutoff frequency that varies as a function of the detected heart rate; and
classifying a pulmonary physiological state to be indicative of at least one of pulmonary obstructive disease, a restrictive respiration disease, rapid shallow non-periodic respiration, and respiration having decreased inhalation duration and increased exhalation duration.

44. The method of claim 43, in which the detecting the time domain thoracic signal includes detecting an impedance signal.

45. The method of claim 43, in which the detecting the time domain thoracic signal includes detecting an acceleration signal.

46. The method of claim 43, in which the transforming the time domain thoracic signal comprises performing a fast Fourier transform (FET).

47. The method of claim 43, in which the filtering includes extracting heart rate contraction information from the frequency domain thoracic signal.

48. The method of claim 43, in which the filtering includes extracting respiration information from the frequency domain thoracic signal.

49. The method of claim 48, further comprising classifying a pulmonary physiological state using the respiration information.

50. The method of claim 49, in which the classifying the pulmonary physiological state includes classifying the pulmonary physiological state as indicative of normal respiration.

51. The method of claim 49, in which the classifying the pulmonary physiological state includes classifying the pulmonary physiological state as indicative of periodic respiration.

52. The method of claim 49, in which the classifying the pulmonary physiological state includes classifying the pulmonary physiological state as indicative of Cheyne-Stokes respiration.

53. The method of claim 49, in which the classifying the pulmonary physiological state includes classifying the pulmonary physiological state as indicative of obstructed respiration.

54. The method of claim 49, in which the classifying the pulmonary physiological state includes classifying the pulmonary physiological state as indicative of restrictive respiration.

55. The method of claim 49, in which the classifying the pulmonary physiological state includes classifying the pulmonary physiological state as indicative of pulmonary fluid accumulation.

56. The method of claim 49, further comprising communicating information about the pulmonary physiological state from within the subject to a remote interface.

* * * * *

UNITED STATES PATENT AND TRADEMARK OFFICE
CERTIFICATE OF CORRECTION

PATENT NO.         : 7,186,220 B2
APPLICATION NO. : 10/612387
DATED               : March 6, 2007
INVENTOR(S)       : Stahmann et al.

Page 1 of 1

It is certified that error appears in the above-identified patent and that said Letters Patent is hereby corrected as shown below:

In column 11, line 45, in Claim 6, delete "(FET)" and insert -- (FFT) --, therefor.

In column 13, line 55, in Claim 31, delete "(FET)" and insert -- (FFT) --, therefor.

In column 14, line 54, in Claim 46, delete "(FET)" and insert -- (FFT) --, therefor.

Signed and Sealed this

Fifteenth Day of May, 2007

JON W. DUDAS
*Director of the United States Patent and Trademark Office*